(12) United States Patent
Atkin et al.

(10) Patent No.: US 7,264,117 B2
(45) Date of Patent: Sep. 4, 2007

(54) ORTHODONTIC PATIENT SET-UP TRAY

(75) Inventors: Gail V. Atkin, Castaic, CA (US); Dick Lee, San Gabriel, CA (US); Oliver L. Puttler, La Crescenta, CA (US); Joan V. Brennan, Sierra Madre, CA (US); James D. Cleary, Glendora, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 452 days.

(21) Appl. No.: 10/804,861

(22) Filed: Mar. 19, 2004

(65) Prior Publication Data

US 2005/0205460 A1    Sep. 22, 2005

(51) Int. Cl.
*B65D 83/10* (2006.01)

(52) U.S. Cl. .................. 206/369; 206/63.5

(58) Field of Classification Search ........... 206/63.5, 206/368, 369, 460, 558, 560, 562, 565, 531, 206/539; 220/4.22; 433/8, 9, 24
See application file for complete search history.

(56) References Cited

U.S. PATENT DOCUMENTS

| | | | |
|---|---|---|---|
| 3,659,706 A * | 5/1972 | Serrell | 206/539 |
| 4,979,611 A | 12/1990 | Bolliger et al. | |
| 5,149,267 A | 9/1992 | Longhini et al. | |
| 5,328,363 A | 7/1994 | Chester et al. | |
| 5,348,154 A | 9/1994 | Jacobs et al. | |
| 5,350,059 A | 9/1994 | Chester et al. | |
| 5,354,199 A | 10/1994 | Jacobs et al. | |
| 5,489,025 A * | 2/1996 | Romick | 206/531 |
| 5,538,129 A | 7/1996 | Chester et al. | |
| 5,636,736 A * | 6/1997 | Jacobs et al. | 206/369 |
| 5,692,896 A | 12/1997 | Pospisil | |
| 6,024,222 A * | 2/2000 | Friberg et al. | 206/531 |
| 6,089,861 A | 7/2000 | Kelly et al. | |
| 6,129,229 A * | 10/2000 | Dunn et al. | 220/4.22 |
| 6,183,249 B1 | 2/2001 | Brennan et al. | |
| 6,213,767 B1 | 4/2001 | Dixon et al. | |
| 6,528,555 B1 | 3/2003 | Nikutowski et al. | |
| 2001/0055741 A1 * | 12/2001 | Dixon et al. | 433/9 |
| 2002/0195363 A1 | 12/2002 | Tuneberg | |
| 2003/0196914 A1 | 10/2003 | Tzou et al. | |
| 2003/0198914 A1 | 10/2003 | Brennan et al. | |
| 2005/0178685 A1 * | 8/2005 | Corcoran et al. | 206/369 |

* cited by examiner

*Primary Examiner*—Luan K. Bui
(74) *Attorney, Agent, or Firm*—James D. Christoff

(57) ABSTRACT

An orthodontic set-up tray includes at least two sections, and each section includes at least one receptacle for receiving an orthodontic appliance. A coupling movably connects the sections together to enable relative movement between the sections. The coupling advantageously permits the overall size of the set-up tray to be reduced or enlarged as may be desired by the practitioner. Optionally, the coupling is a releasable coupling that enables the sections to be detached from one another.

36 Claims, 6 Drawing Sheets

ORTHODONTIC PATIENT SET-UP TRAY

BACKGROUND OF THE INVENTION

1. Field of the Invention

This invention broadly relates to a tray used in orthodontic offices for holding appliances that are used during the course of treatment. More particularly, the present invention is directed to an orthodontic set-up tray having receptacles that removably receive appliances intended for connection to the teeth of an orthodontic patient.

2. Description of the Related Art

Orthodontic treatment involves movement of malpositioned teeth to improved positions in proper alignment with each other. Orthodontic treatment can enable the patient's teeth to function better with each other during mastication. In addition, orthodontic treatment can greatly enhance the patient's facial appearance, especially in regions near the front of the patient's oral cavity.

One type of common orthodontic treatment includes the use of a set of tiny appliances known as brackets. Each bracket is received on a respective tooth of the patient, and has a slot for receiving a resilient wire known as an archwire. The archwire forms a track to guide movement of the teeth to orthodontically correct positions. Ends of the archwire are often received in small appliances known as buccal tubes that are connected to the patient's molar teeth.

Each of the patient's teeth has a configuration that is different than other teeth in the oral cavity. In addition, the desired final orientation of each tooth in three-dimensional space, such as the amount of inclination of the longitudinal axis of the tooth as well as the position of the longitudinal axis relative to a particular reference point in the patient's oral cavity, differs from one tooth to another. The orthodontic appliances that are selected for each patient typically vary in structural geometry from one another and are intended for use only with certain teeth.

Orthodontic appliances that are selected by the practitioner for use with a particular patient are often placed in advance on a tray known as a set-up tray. The set-up tray has receptacles for receiving the appliances and arranging the appliances in an orderly fashion. By arranging the appliances in the receptacles in advance, the selection and placement of the appliances is facilitated once the patient's teeth have been properly prepared.

Orthodontic set-up trays often have receptacles arranged along two rows. The receptacles in the upper row correspond in location to teeth located along the patient's upper dental arch, and the receptacles in the lower row correspond in location to teeth that are located along the patient's lower dental arch. In this manner, the appliances can be quickly retrieved in the order desired by the practitioner and there is less likelihood that one of the appliances will be placed on a tooth other than the intended tooth.

Many orthodontic set-up trays have two rows of receptacles with fourteen receptacles in each row for a total of twenty-eight receptacles, and are normally used by placing an appliance in each receptacle so that an appliance is provided for each tooth of the patient's upper and lower dental arches. Other orthodontic set-up trays have two rows of receptacles with ten receptacles in each row for a total of twenty receptacles, and are normally used in a similar fashion except that appliances for the molar teeth are omitted. If the practitioner elects to use a set-up tray having only twenty receptacles, the appliances intended for the molar teeth are typically handled separately.

A variety of orthodontic set-up trays are known. Some set-up trays are intended for use with a single patient, and other set-up trays are intended for reuse. Orthodontic set-up trays intended for reuse are typically disinfected or sterilized after each use in order to reduce the likelihood of cross-contamination between patients. If the reusable tray is sterilized, it is often sterilized in the same equipment used to sterilize other articles in the practitioner's office such as hand instruments.

Unfortunately, many of the orthodontic set-up trays with twenty-eight receptacles do not fit within the confines of the sterilizer in the practitioner's office. The purchase of a larger sterilizer may not be an attractive option due to the expense. Moreover, reducing the size of a set-up tray with twenty-eight receptacles may not be a satisfactory solution for some practitioners, because the space between each receptacle is reduced. This reduction in space tends to increase the difficulty of grasping the appliance when needed for use.

SUMMARY OF THE INVENTION

The present invention is directed toward an orthodontic patient set-up tray that can be adapted in size according to the practitioner's preferences. For example, the configuration of the set-up tray can be modified when desired to fit within the confines of conventional dental sterilizers. The configuration of the set-up tray may also be modified by increasing or decreasing the quantity of available receptacles, so that the tray can be made smaller and more easily handled in the operatory when all of the receptacles are not needed.

In more detail, the present invention is directed to an orthodontic patient set-up tray that comprises a first section having at least one receptacle for receiving an orthodontic appliance. The set-up tray also includes a second section having at least one receptacle for receiving an orthodontic appliance. A coupling movably connects the first section to the second section to enable relative movement between the first section and the second section.

The invention includes multiple aspects. In one aspect, the coupling is a releasable coupling that enables the first and second sections to be disconnected from each other when desired. In another aspect, the coupling pivotally connects the first section to the second section to enable, for example, the sections to be folded together and form a relatively compact configuration. The receptacles of the set-up tray may be constructed to receive the appliances alone, or alternatively constructed to receive containers that each contains a single appliance.

The present invention is also directed toward an orthodontic patient set-up tray that comprises a substrate having two spaced-apart projections and a receptacle located between the projections. Each projection includes an overhanging section that provides an undercut region adjacent the receptacle for releasably retaining a container that contains an orthodontic appliance.

These and other features of the invention are described in more detail in the paragraphs that follow and are illustrated in the accompanying drawings.

DETAILED DESCRIPTION OF THE PREFERRED EMBODIMENTS

Figure 1:
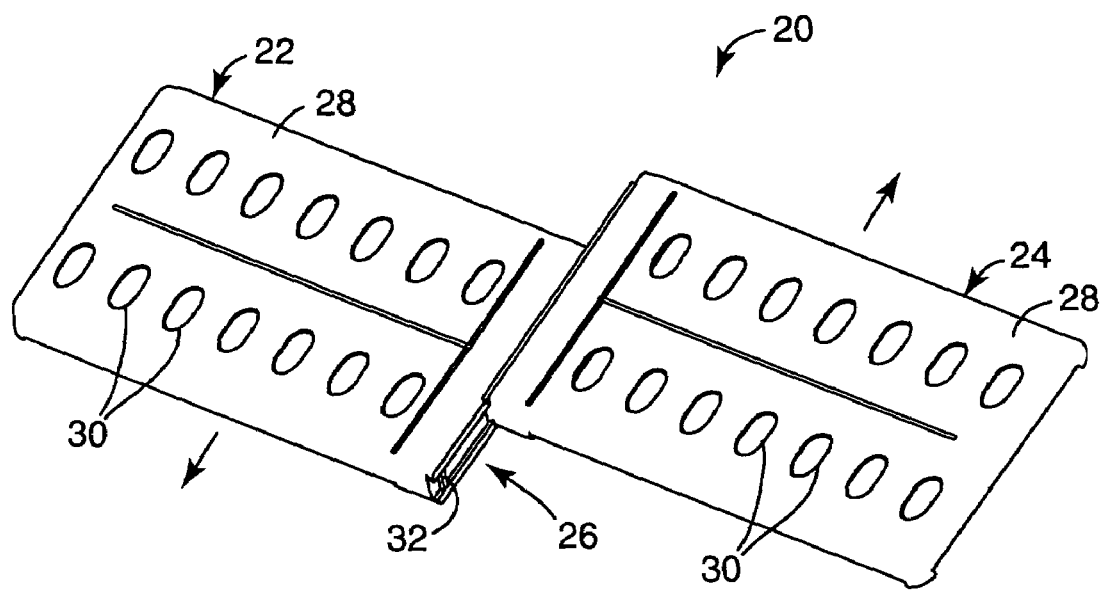
FIG. 1 is a top, front and right side perspective view of an orthodontic patient set-up tray according to one embodiment of the present invention, wherein a first section and a second section of the tray are shown in relative positions as they might appear during the act of coupling or uncoupling the sections together.

An orthodontic patient set-up tray that is constructed in accordance with one embodiment of the present invention is illustrated in FIGS. 1-6 and is broadly designated by the numeral 20. The set-up tray 20 includes a first elongated section 22 and a second elongated section 24. A coupling 26 movably connects the first section 22 to the second section 24 to enable relative movement between the first section 22 and the second section 24.

In more detail, each of the first and second sections 22, 24 includes a substrate 28 having a generally planar configuration. Each substrate 28 includes at least one receptacle 30 for receiving an orthodontic appliance. In the illustrated embodiment, the receptacles 30 are openings formed in the substrate 28, although other constructions are also possible.

The first and second sections 22, 24 each contain an array with two rows of receptacles 30, and each row preferably includes seven receptacles 30. Each receptacle 30 corresponds to a particular tooth in the patient's oral cavity. In particular, and with reference to FIGS. 1 and 2, the first section 22 includes an upper row of receptacles 30 for receiving appliances for each tooth of the patient's upper right area or quadrant, extending from the upper right second molar to the upper right central incisor. The first section 22 also includes a lower row of seven receptacles 30 corresponding to the teeth of the patient's lower right area or quadrant, extending from the patient's lower right second molar tooth to the patient's lower right central incisor tooth. Likewise, the second section 24 includes an upper row of seven receptacles 30 to receive appliances for each tooth of the patient's upper left dental area or quadrant, extending from the upper second left molar tooth to the upper left central incisor. The second section 24 also includes a lower row of receptacles 30 to receive appliances for the patient's lower left dental area or quadrant, extending from the lower second left molar tooth to the lower left central incisor tooth.

Figure 4:
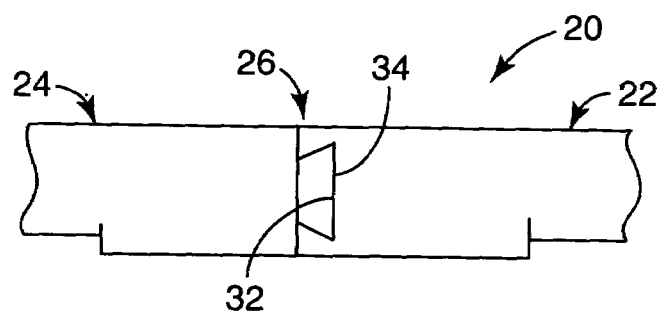
FIG. 4 is a fragmentary, enlarged rear elevational view of a portion of the tray shown in FIG. 3, depicting a coupling of the tray for connecting the first and second sections together.

The coupling 26 of the set-up tray 20 is shown in enlarged view in FIG. 4. In this embodiment, the coupling 26 is a slide coupling. The first section 22 has an elongated dovetail-shaped groove 32 extending along one end of the substrate 28, and the second section 24 includes an elongated dove-tail-shaped tongue 34 that extends along an adjacent end of the substrate 28. The tongue 34 and the groove 32 have mating configurations and together represent the coupling 26.

Figure 2:
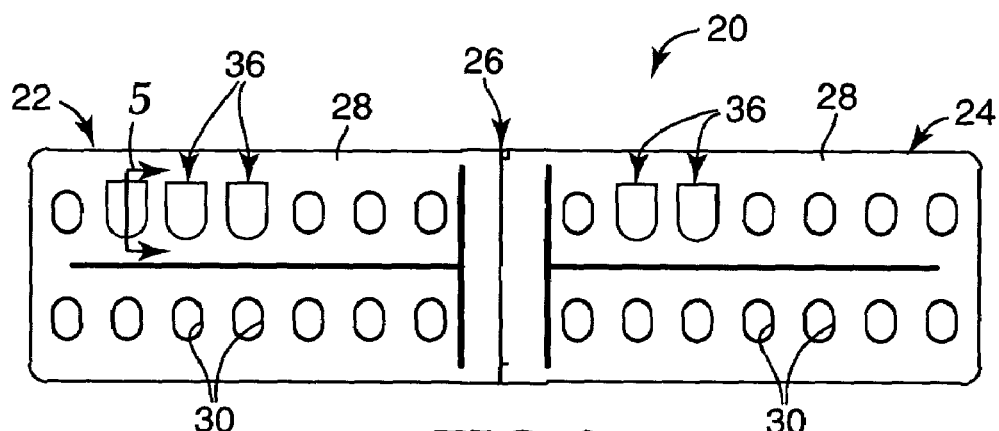
FIG. 2 is a plan view of the set-up tray shown in FIG. 1, wherein the first and second sections are shown fully assembled as they might appear during use of the tray, and wherein are also shown for purposes of illustration five containers that have been received in five receptacles of the tray.
Figure 3:
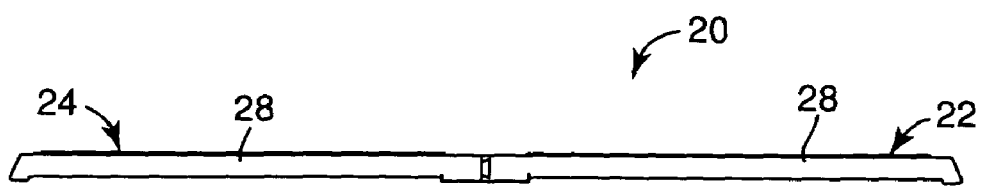
FIG. 3 is a front elevational view of the set-up tray shown in FIG. 2.

Preferably, the coupling 26 includes structure presenting a "click-lock" feature that provides tactile feedback to the user that the sections 22, 24 have been fully assembled to each other and arranged in the aligned, coupled-together configuration shown in FIG. 2. The click-lock structure may be provided, for example, by a protrusion located along the groove 32 or the tongue 34 that fits within a recess located along the other of the groove 32 or the tongue 34 when the sections 22, 24 are fully assembled to each other. The click-lock structure securely holds the sections 22, 24 together during use and normal handling, but are appropriately sized to release from each other when desired upon the presence of sufficient hand force as the sections 22, 24 are disassembled from each other.

To disassemble the tray 20, the user urges the sections 22, 24 in directions perpendicular to the longitudinal axes of the sections 22, 24 and parallel to the upper flat surface of the substrate 28. These directions are shown by the arrows in FIG. 1. As the sections 22, 24 are so urged, the protrusion escapes from the recess and the tongue 34 and the groove 32 slide relative to each other in directions parallel to the arrows. Continued sliding movement of the sections 22, 24 disconnects the same as may be desired, for example, when the user intends to handle the sections 22, 24 separately or attempts to fit the tray within the confines of a relatively small sterilizer.

In this embodiment, the opening of each receptacle 30 is adapted to receive a container that holds an orthodontic appliance such as a bracket or buccal tube. For purposes of illustration, five containers 36 are illustrated in FIG. 2, each received in a respective one of the receptacles 30. In practice, however, the practitioner will often place a container 36 in each receptacle 30 corresponding to the patient's teeth, so that an appliance is pre-designated for each tooth and ready for use.

Figure 5:
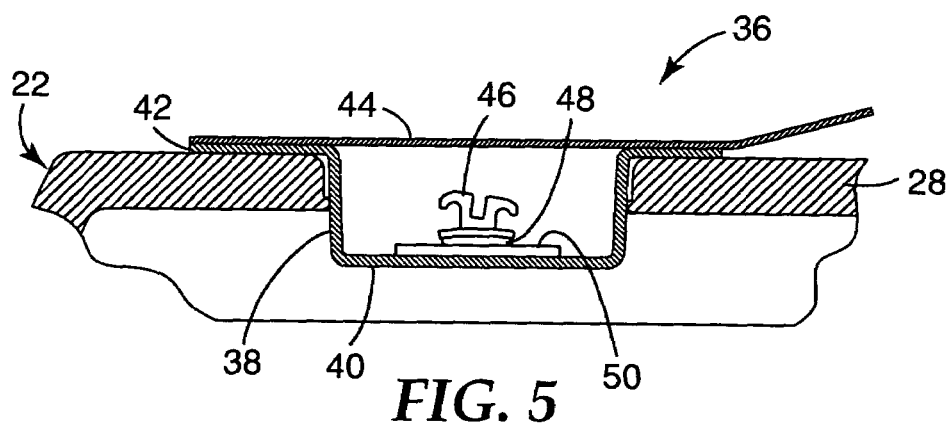
FIG. 5 is an enlarged side cross-sectional view taken along lines 5-5 of FIG. 2, illustrating a portion of the tray, one of the containers and an appliance received in the tray.
Figure 6:
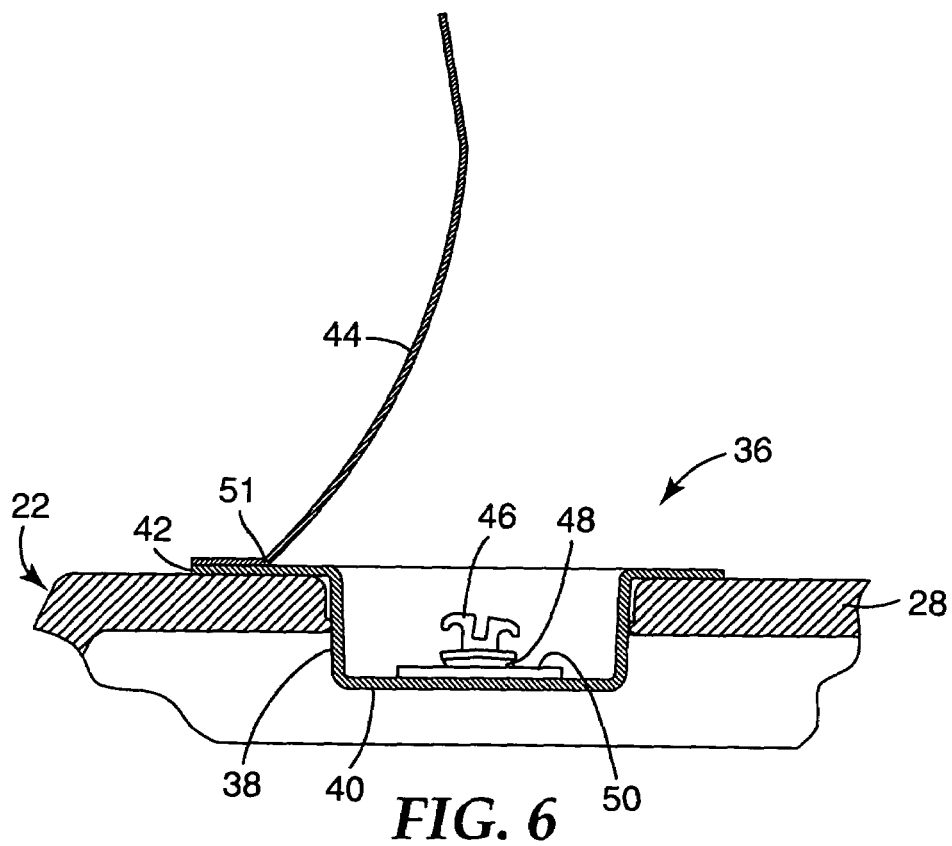
FIG. 6 is a view somewhat similar to FIG. 5 except that a cover of the container has been moved to an open position.

FIGS. 5 and 6 illustrate an exemplary container 36. Each container 36 has an upright sidewall 38 that has an oval-shaped configuration in plan view. An oval-shaped bottom 40 is integrally connected to the sidewall 38, and the bottom 40 together with the sidewall 38 define a well. The sidewall 38 is also connected to a rectangular top flange 42, and a cover 44 is releasably connected to the flange 42 by an adhesive.

The sidewall 38 is received in the opening of the receptacle 30, and a friction fit between the sidewall 38 and the periphery of the opening comprises a means for releasably retaining the container 36 in the receptacle 30. Other retaining means are also possible, such as recesses in the sidewall 38 that snap-fit into the edge of the opening.

An orthodontic appliance 46 is received in the container 36. Preferably, a base of the appliance 46 is pre-coated with a layer of orthodontic adhesive 48 for directly bonding the appliance 46 to the enamel surface of a patient's tooth. Preferably, the adhesive 48 is a light-curable, non-toxic adhesive paste that is in releasable contact with a release surface 50. Suitable adhesives are described, for example, in U.S. Pat. Nos. 5,354,199 and 6,528,555 and published U.S. Patent Application No. 2003/0198914. Suitable release surfaces are described, for example, in U.S. Pat. Nos. 5,328,363 and 6,183,249.

In FIG. 5, the cover 44 is shown in a closed position. In FIG. 6, the cover 44 is shown in an open position. Once the cover 44 has been opened, the practitioner may grasp the appliance 46 with a hand instrument such as a tweezers or bracket placement tool in order to lift the appliance 46 from the release surface 50 and withdraw the appliance 46 from the well for attachment to the pre-designated tooth of the orthodontic patient.

Preferably, the container 36 provides a substantial barrier to the transmission of water vapor and light in order to protect the adhesive 48. Suitable materials for making the container 36 are described, for example, in U.S. Pat. No. 5,328,363 and published U.S. Patent Application No. 2003/0196914. Other containers are also possible. However, the use of containers is optional. For example, each receptacle 30 may comprise a well that directly receives an appliance that is not surrounded by a container. Optionally, each well is initially sealed by, for example, a clear plastic film that extends over a single well or a multiple number of wells.

Figure 7:
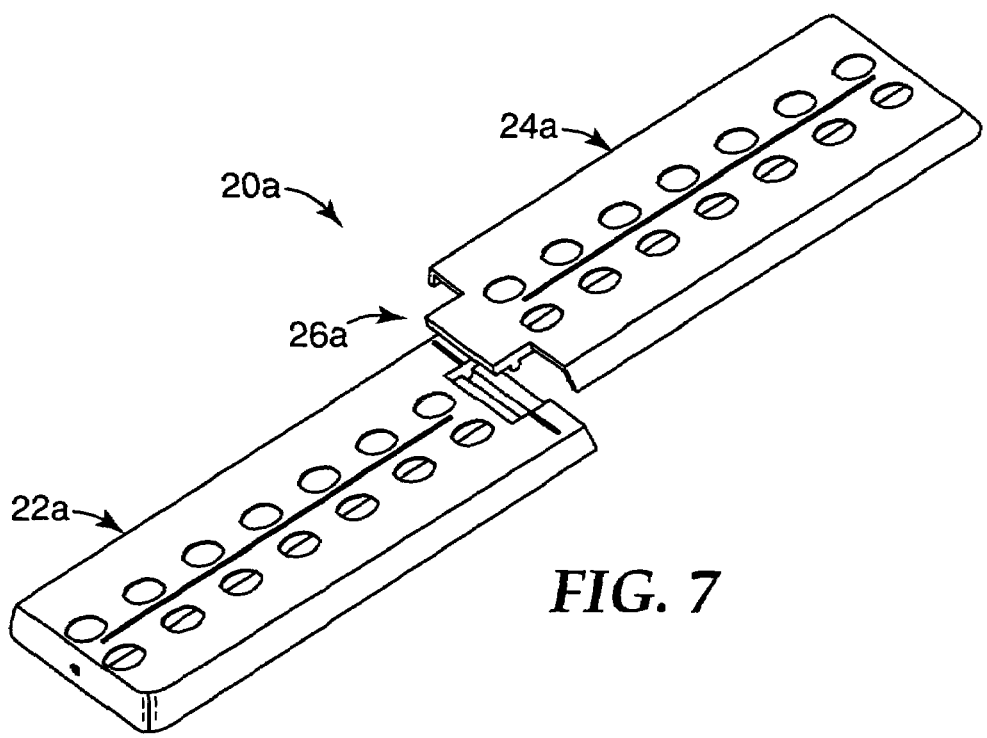
FIG. 7 is a top, front and left side perspective view of an orthodontic patient set-up tray according to another embodiment of the invention.
Figure 8:
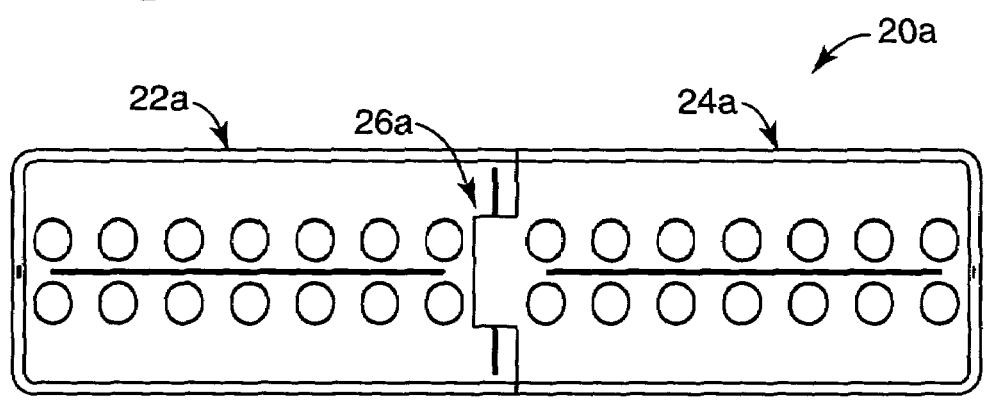
FIG. 8 is a plan view of the set-up tray shown in FIG. 7, illustrating the tray as it might appear when first and second sections of the tray are assembled together.
Figure 9:
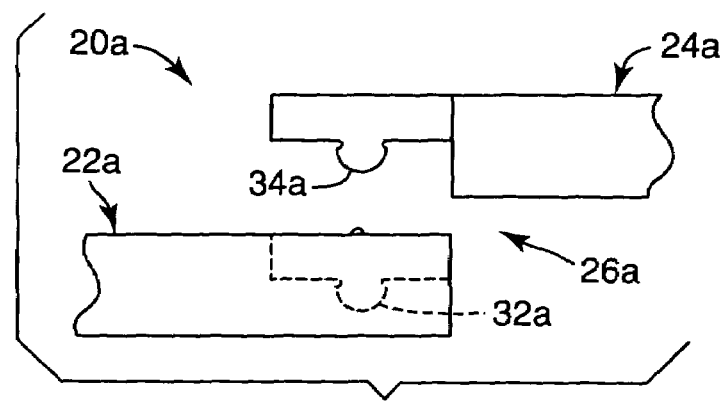
FIG. 9 is a fragmentary, enlarged front elevational view of the tray shown in FIG. 7, illustrating a coupling of the tray for releasably connecting the first and second sections of the tray together.

An orthodontic patient set-up tray 20a according to another embodiment of the invention is illustrated in FIGS. 7-9. Except as described below, the set-up tray 20a is similar to the tray 20 described in connection with FIGS. 1-6. As such, a detailed description of the common aspects need not be repeated.

The set-up tray 20a has a first section 22a, a second section 24a and a coupling 26a for movably connecting the first and second sections 22a, 24a. However, the coupling 26a is somewhat different than the coupling 26 mentioned above. In this embodiment, the coupling 26a includes a groove 32a and a tongue 34a, and the sections 22a, 24a are assembled together by relative movement toward each other in directions perpendicular to the upper flat surface of the sections 22a, 24a.

Preferably, the coupling 26a is constructed to snap together by finger pressure. To this end, both the groove 32a and the tongue 34a have a cross-sectional shape in the form of a partial circle with two undercut regions. The sections 22a, 24a are made of a material that has sufficient resiliency to enable one or both of the groove and tongue 32a, 34a to slightly deform as the sections 22a, 24a are pressed together in order to snap-fit the tongue 34a into the groove 32a. This snap-fit relationship subsequently maintains the sections 22a, 24a in assembled relation until disconnected by the practitioner.

Other snap-fit constructions are also possible. For example, the coupling could comprise a series of projections extending from one end of one of the sections, and a mating series of holes that are provided in the adjacent end of the other section. Other releasable connections include hook and loop fasteners, magnets and the like.

Figure 10:
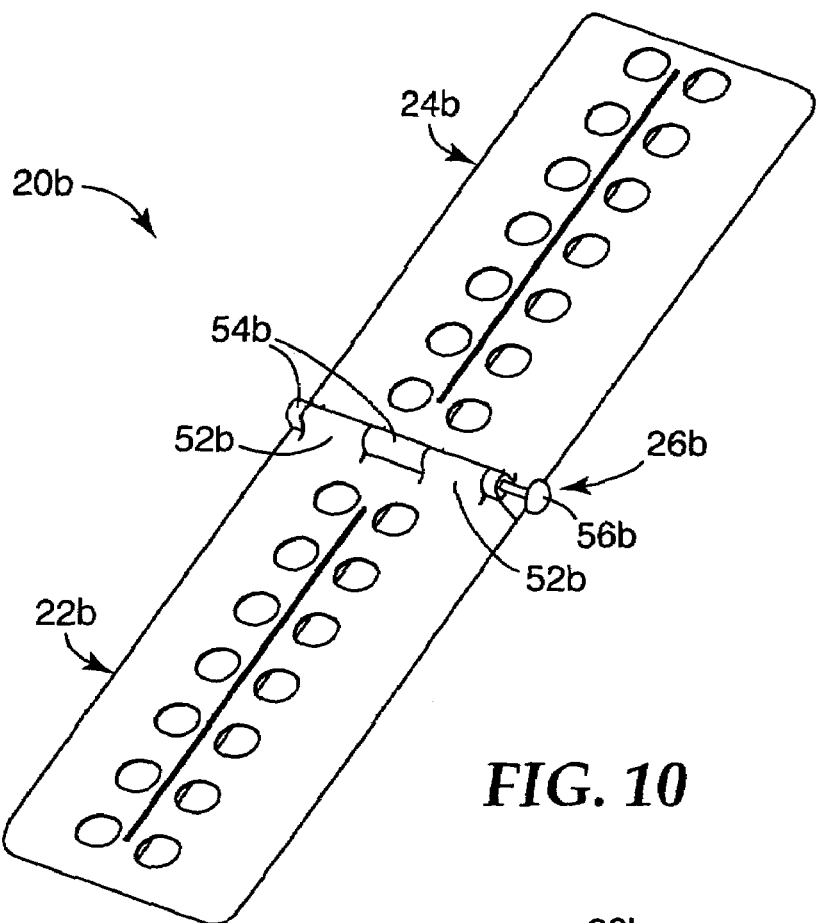
FIG. 10 is a top, front and left side perspective view of an orthodontic patient set-up tray according to another embodiment of the invention.
Figure 11:
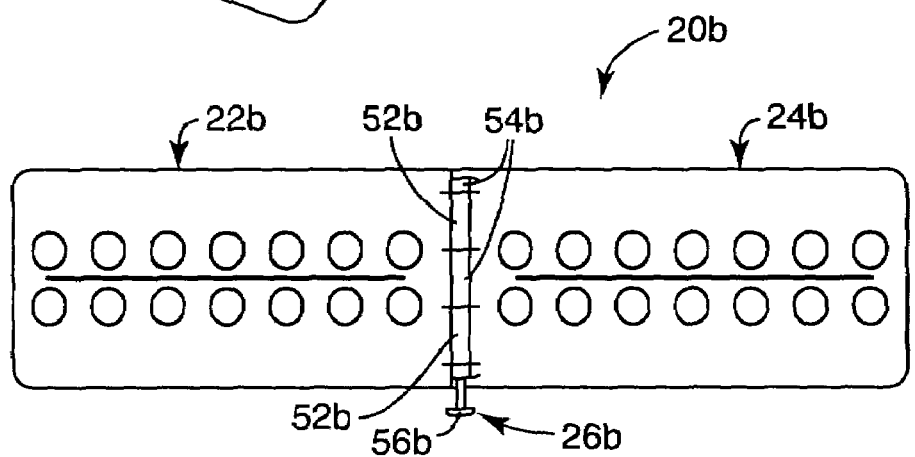
FIG. 11 is a plan view of the set-up tray shown in FIG. 10.
Figure 12:
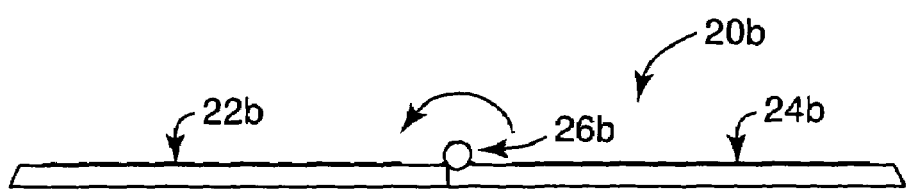
FIG. 12 is a front elevational view of the set-up tray shown in FIGS. 10 and 11.

An orthodontic patient set-up tray 20b according to another embodiment of the invention is illustrated in FIGS. 10-12. The set-up tray 20b is similar to the set-up tray 20 except as described below.

The set-up tray 20b includes a first section 22b and a second section 24b. A coupling 26b movably connects the first section 22b to the second section 24b for enabling relative movement between the sections 22b, 24b. In this embodiment, the coupling 26b comprises a hinge.

The coupling 26b includes two cylindrical portions 52b that are connected to the first section 22b, and three cylindrical portions 54b that are connected to the second section 24b. When the sections 22b, 24b are assembled together as shown in FIGS. 10-12, the cylindrical portions 52b, 54b extend in aligned relationship along a common axis. Each of the cylindrical portions 52b, 54b includes a bore, and the bores together present a common straight passage.

The coupling 26b also includes a pin 56b having a shank that is received in the bores of the cylindrical portions 52b, 54b. The pin 56b has an enlarged head as shown in the drawings. The coupling 26b enables the sections 22b, 24b to pivotally move in an arc as shown by the arrow in FIG. 12 to a relatively compact, folded configuration when desired.

Optionally, the pin 56b is removable from the bores of the cylindrical portions 52b, 54b in order to enable the sections 22b, 24b to disengage each other. Alternatively, the pin may be constructed as a "tight" pin that cannot readily be removed from the bores by the user.

Figure 13:
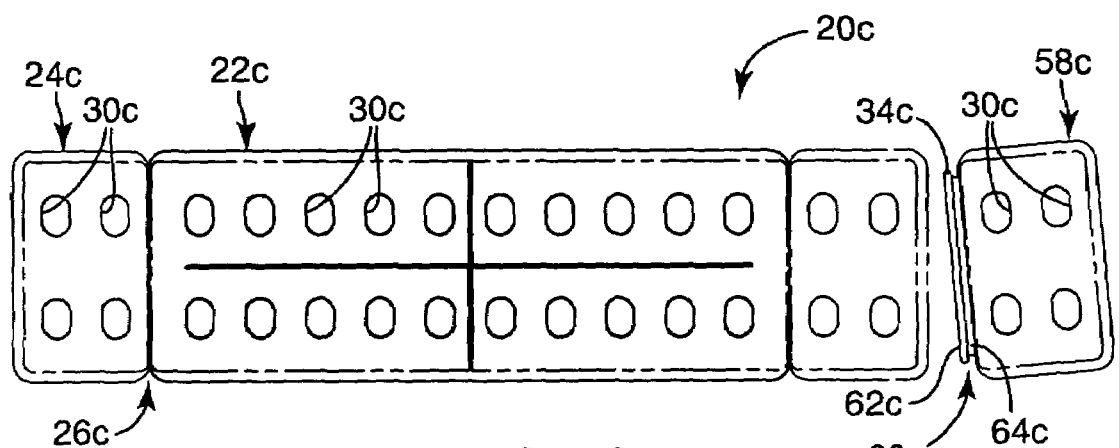
FIG. 13 is a plan view of an orthodontic set-up tray according to still another embodiment of the invention, wherein the tray includes three sections, and wherein one section of the tray is shown as it might appear when disconnected from the other two sections.

An orthodontic patient set-up tray 20c according to another embodiment of the invention is illustrated in FIG. 13. Except as described below, the set-up tray 20c is similar to the set-up tray 20 mentioned above.

The set-up tray 20c includes a first section 22c, a second section 24c as well as a third section 58c. In the illustrated embodiment, the first section 22c has two rows of receptacles 30c, including an upper row of ten receptacles 30c and a lower row of ten receptacles 30c. The receptacles 30c of the first section 22c are intended to receive appliances for the non-molar teeth of the upper and lower dental arches.

The second section 24c and the third section 58c each include an upper and lower row of receptacles 30c, and two receptacles 30c are provided in each row. The receptacles 30c of the sections 24c, 58c are intended to receive appliances for connection to the patient's molar teeth. In particular, the four receptacles 30c of the second section 24c are intended to receive molar appliances for the upper and lower, first and second molar teeth on the right side of the patient's dental arch, while the receptacles 30c of the third section 58c are intended to receive appliances for the upper and lower, first and second molar teeth on the left side of the patient's dental arches.

A coupling 26c movably connects the first section 22c and the second section 24c, and preferably is a releasable coupling that enables the sections 22c, 24c to be separated when desired. Similarly, a second coupling 60c movably connects the first section 22c and the third section 58c, and preferably is a releasable coupling for enabling the first section 22c to be disengaged from the third section 58c when desired.

The couplings 26c, 60c preferably have a snap-fit construction. In this embodiment, each end of the first section 22c includes an elongated groove or aperture (not shown)

that releasably receives a matching tongue 34c. The tongue 34c includes an outermost lip 62c as well as an adjacent, somewhat smaller neck portion 64c. The lip 62c is somewhat larger than the aperture of the first section 22c, and once forced through the aperture, retains the sections 22c, 58c together.

In FIG. 13, the third section 58c is illustrated in full line view as it might appear when disconnected from the first section 22c. FIG. 13 also illustrates in dashed line view the position of the third section 58c when the second coupling 60c connects the sections 22c, 58c together. The coupling 26c is not shown in detail, but preferably is similar to the coupling 60c.

The patient set-up tray 20c shown in FIG. 13 is especially useful in orthodontic practices where some but not all of the patients are designated to receive molar appliances that are directly bonded to the patient's teeth. Directly bonded molar appliances may be provided, for example, in containers similar to the containers 36 shown in FIGS. 5 and 6. However, patients that are designated to receive molar appliances that are not directly bonded to the patient's teeth may instead receive molar appliances that are mounted on orthodontic bands, and it is possible that such appliance and band assemblies are too large to fit within containers such as containers 36. In those instances, the appliance and band assemblies may be provided separately, or alternatively provided in larger containers that are received in sections that are similar to the sections 24c, 58c but somewhat larger in order to accommodate the increased size of the containers.

Figure 14:
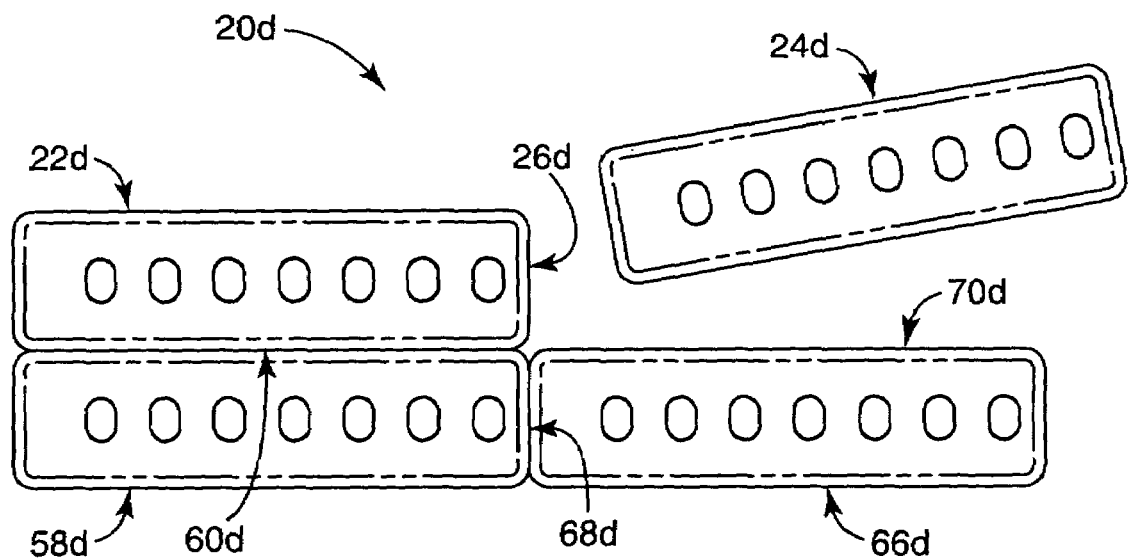
FIG. 14 is a plan view of an orthodontic patient set-up tray having four sections according to yet another embodiment of the invention, wherein one of the sections has been detached from the remaining sections.

An orthodontic patient set-up tray 20d according to another embodiment of the invention is illustrated in FIG. 14. Except as described below, the set-up tray 20d is similar to the set-up tray 20 set out above.

The set-up tray 20d includes a first section 22d, a second section 24d, a third section 58d and a fourth section 66d. As shown in FIG. 14, each of the sections 22d, 24d, 58d, 66d has a single roll of seven receptacles 30d. Alternatively, each of the sections 22d, 24d, 58d, 66d may contain a single row of five receptacles 30d.

A coupling 26d movably connects the sections 22d, 24d together and enables relative movement between the sections 22d, 24d. In this embodiment, the coupling 26d is a line of weakness that extends along adjacent ends of the sections 22d, 24d. The line of weakness may present a "living hinge" that enables pivotal movement of the sections 22d, 24d in an arc about the line of weakness. In addition to, or alternatively, the line of weakness may present a region between the sections 22d, 24d that can be readily ruptured to disconnect the sections 22d, 24d from each other.

A second coupling 60d movably connects the first section 22d to the third section 58d. Similarly, a third coupling 68d movably connects the third section 58d to the fourth section 66d. Also, a fourth coupling 70d movably connects the second section 24d to the fourth section 66d.

Preferably, the couplings 60d, 68d, 70d are similar in construction and function to the coupling 26d. Optionally, the couplings 26d, 60d, 68d, 70d may be manufactured by integrally molding the tray 20 as an initially unitary component, with each of the couplings 26d, 60d, 68d, 70d made by forming a relatively thin web between the respective, adjacent sections. As another alternative, the couplings may be made using a series of perforations or by using a knife blade to form one or more indents.

Figure 15:
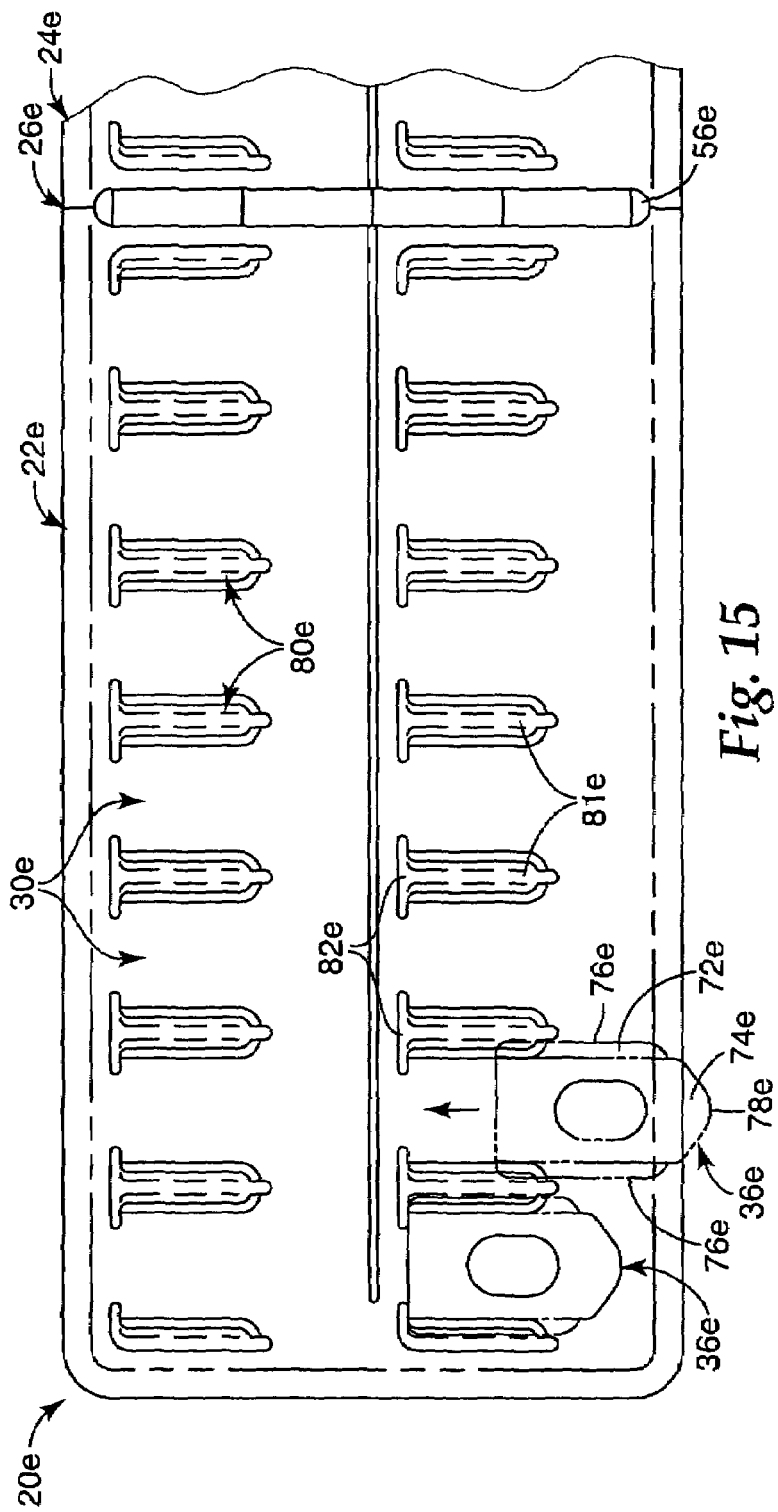
FIG. 15 is a fragmentary plan view of an orthodontic patient set-up tray according to an additional embodiment of the invention.
Figure 16:
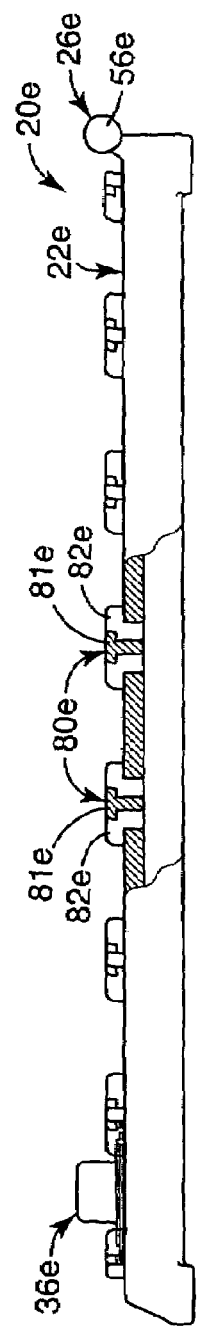
FIG. 16 is a front elevational view in partial section of a portion of the set-up tray illustrated in FIG. 15.

An orthodontic patient set-up tray 20e according to another embodiment of the invention is illustrated in FIGS. 15 and 16. The set-up tray 20e includes a first section 22e and a second section 24e (shown in FIG. 15 only). A coupling 26e movably connects the first section 22e and the second section 24e.

The coupling 26e is somewhat similar to the coupling 26b shown in FIGS. 10-12, and enables pivotal relative movement of the sections 22e, 24e in an arc about the longitudinal axis of a pin 56e. In this embodiment, the pin 56e is a tight pin that cannot be readily removed.

Each of the tray sections 22e, 24e includes a substrate and has two rows of seven receptacles 30e. The receptacles are adapted to releasably receive a container 36e that, in turn, contains an orthodontic appliance such as a bracket or buccal tube. Optionally, the appliance (not shown) within the container 36e has a layer of photopolymerizable adhesive that is preapplied to a base of the appliance by the manufacturer.

The containers 36e include a flat bottom support 72e as well as a dome-shaped member 74e that extends over the support 72e. As illustrated in FIGS. 15 and 16, the support 72e extends beyond the member 74e in either directions along the longitudinal axis of the section of the tray section 22e and presents two edge portions 76e. Preferably, the dome-shaped member 74e also extends beyond the support 72e in a direction parallel to the edge portions 76e in order to provide a finger-engageable tab 78e.

Each of the tray sections 22e, 24e includes elongated projections or rails 80e that extend on opposite sides of each receptacle 30e. As shown in FIG. 16, the rails 80e include a top segment 81e with opposed overhanging sections that provide an undercut region extending along each side of the rail 80e. Preferably, the length of each rail 80e is at least as great as one-half of the length of the edge portions 76e.

Each container 36e is inserted into a respective receptacle 30e by movement in a direction along the arrow that is shown in FIG. 15. As the container 36e is moved into the receptacle 30e, the edge portions 76e are received in the undercut regions presented by adjacent rails 80e. Movement of the container 36e continues until reaching a stop that is provided by an end portion of the rail 80e, designated by the numeral 82e in FIG. 15.

The distance between the outermost edges of the edge portion 76e is less than the center-to-center distance between the rails 80e, but is greater than the distance between the top segment 81e of adjacent rails 80e. As a consequence, the overhanging sections of the top segments 81e releasably retain the container 36e on the tray 20e. When desired, the container 36e may be removed from its receptacle 30e by movement in a direction opposite to the direction of the arrow depicted in FIG. 15.

The container 36e is opened by lifting the dome-shaped member 74e through the space between the projections 80e and in a direction away from the support 72e. As the member 74e is lifted, the member 74e detaches from the support 72e to expose the appliance within the container 36e. Optionally, the container 36e may be constructed so that the member 74e completely detaches from the support 72e as the member 74e is lifted. As another option, one end of the member 74e (such as the end adjacent the end portion 82e) may be connected to the support 72e by a hinged arrangement such as a line of weakness similar to the line of weakness 51 illustrated in FIG. 6.

The rails 80e constitute structure for releasably retaining the containers 36e in the receptacles 30e as may be desired. The rails 80e retain the support 72e in place, not only during handling of the tray 20e but also during the time that the dome-shaped member 74e is opened to provide access to the appliance within.

The set-up trays as described above in the various embodiments may be constructed from a variety of materials including plastics (such as "Vectra" brand liquid crystal polymer, from Tacona GmbH) and metallic materials (such as stainless steel or aluminum). Optionally, the set-up tray, and particularly the set-up tray 20d may be made of boxboard, chip board or moldable paper pulp material. The set-up trays may also optionally include receptacles having a shape to receive other items, such as a hand instrument or a container having a quantity of primer or etchant used in the bonding procedure.

As another option, the tray (such as tray 20d) may be provided with means for releasably connecting to appliances that are not received in containers. For example, each of the receptacles may be in the shape of a well with a pressure sensitive adhesive extending along the bottom of each well. Optionally, each section of the tray may include an upper layer having a series of apertures representing the receptacles, an intermediate film layer that is coated along one side with a pressure sensitive adhesive or covered with a foam tape, and a bottom layer having a smooth flat upper surface. In this example, the appliances are preferably not coated in advance with an orthodontic bonding adhesive, but instead receive the bonding adhesive once the practitioner has lifted the appliance from the adhesive film.

As an additional option, the receptacles in any of the trays described above may have shapes that differ from one another in order to assure that only certain containers could be received in particular receptacles. For example, the receptacles located along the upper row and corresponding to the patient's upper teeth may have a generally round configuration in plan view, while the receptacles extending along the lower row and corresponding to the patient's lower teeth may have an oval-shaped configuration in plan view. Similarly, the containers containing appliances designated for the patient's upper teeth may have a bottom portion that is round to matingly fit in the round receptacles of the upper row. The bottom portion of the containers containing appliances for the lower teeth may have an oval configuration that cannot fit in the round receptacles of the upper row, but only in the oval-shaped receptacles of the lower row. In this manner, there is less likelihood that appliances intended for the patient's lower teeth will be attached by the practitioner to the patient's upper teeth in error.

A number of other alternatives are also possible. For example, the couplings 26c, 60c described in connection with FIGS. 13 and 14 may comprise a living hinge. Moreover, any of the trays described above may be constructed with a single row of receptacles for use with only the upper teeth of a patient's dental arch or for use only with the lower teeth of the patient's dental arch.

All of the patents and/or patent applications mentioned above are hereby expressly incorporated by reference herein. The embodiments described above are intended to exemplify aspects of the invention, and the invention should not be deemed limited to the particular embodiments illustrated. Instead, the invention should only be limited by a fair scope of the claims that follow along with their equivalents.

The invention claimed is:

1. An orthodontic patient set-up tray comprising:
a first section having a first array of receptacles, wherein the first array of receptacles is arranged in two rows corresponding to a first area of a patient's upper and lower dental arches;
a first orthodontic appliance received in a first receptacle of the first array;
a second section having a second array of receptacles, wherein the second array of receptacles is arranged in two rows corresponding to a second area of a patient's upper and lower dental arches;
a second orthodontic appliance received in a second receptacle of the second array; and
a coupling movably connecting the first section to the second section to enable relative movement between the first section and the second section.

2. An orthodontic patient set-up tray according to claim 1 wherein the coupling is a releasable coupling for selectively disconnecting the first section from the second section.

3. An orthodontic patient set-up tray according to claim 2 wherein the coupling comprises a hinge having a pin.

4. An orthodontic patient set-up tray according to claim 2 wherein the coupling comprises a tongue and a groove.

5. An orthodontic patient set-up tray according to claim 4 wherein the first section and the second section each have a longitudinal axis, and wherein the tongue and the groove each have respective longitudinal axes that extend in directions perpendicular to the longitudinal axes of the first and second sections.

6. An orthodontic patient set-up tray according to claim 2 wherein the coupling is a slide coupling.

7. An orthodontic patient set-up tray according to claim 2 wherein the coupling has a snap-fit construction.

8. An orthodontic patient set-up tray according to claim 2 wherein the coupling comprises a line of weakness.

9. An orthodontic patient set-up tray according to claim 1 wherein the coupling pivotally connects the first section to the second section.

10. An orthodontic patient set-up tray according to claim 9 wherein the coupling comprises a hinge with a first section and a second section, and wherein the hinge includes a removable pin for selectively disconnecting the first section and the second section.

11. An orthodontic patient set-up tray according to claim 9 wherein the coupling comprises a line of weakness.

12. An orthodontic patient set-up tray according to claim 9 wherein the first section and the second section each have a longitudinal axis, wherein the longitudinal axes of the first section and the second section extend in generally parallel directions, and wherein the coupling connects the first section and the second section for pivotal movement in an arc about an axis generally perpendicular to the longitudinal axes of the first section and the second section.

13. An orthodontic patient set-up tray according to claim 1 wherein the coupling comprises a tongue and a groove.

14. An orthodontic patient set-up tray according to claim 13 wherein the tongue is constructed to fit into the groove in snap-fit relation.

15. An orthodontic patient set-up tray according to claim 13 wherein the first section and the second section each have a longitudinal axis, wherein the longitudinal axes of the first section and the second section extend in generally parallel directions, and wherein the groove extends in a direction generally perpendicular to the longitudinal axes of the first section and the second section.

16. An orthodontic patient set-up tray according to claim 15 wherein the first and second sections generally extend in a flat reference plane, and wherein the tongue is constructed to fit into the groove by relatively moving the first section and the second section toward each other in directions perpendicular to the reference plane.

17. An orthodontic patient set-up tray according to claim 1 wherein the receptacle comprises an opening.

18. An orthodontic patient set-up tray according to claim 1 wherein each receptacle includes means for releasably retaining a container.

19. An orthodontic patient set-up tray according to claim 18 wherein the receptacle comprises an opening, and wherein the means comprises a friction fit.

20. An orthodontic patient set-up tray according to claim 1 and including a first container received in the first receptacle and a second container received in the second receptacle, and wherein the first appliance is received in the first container and the second appliance is received in the second container.

21. An orthodontic patient set-up tray according to claim 1 and including an additional plurality of orthodontic appliances, wherein each receptacle receives a corresponding appliance.

22. An orthodontic patient set-up tray according to claim 20 wherein each container also includes an adhesive in contact with the appliance.

23. An orthodontic patient set-up tray according to claim 1 wherein the first array and the second array each include fourteen receptacles with seven receptacles in each row.

24. An orthodontic patient set-up tray according to claim 1 and including a third section and a second coupling movably connecting the third section to the first section.

25. An orthodontic patient set-up tray according to claim 24 wherein the first section has ten receptacles corresponding to non-molar teeth of the patient, and wherein the second section and the third section each include four receptacles corresponding to the molar teeth of the patient.

26. An orthodontic patient set-up tray comprising a substrate having two spaced-apart projections and a receptacle located between the projections, each projection including an overhanging section that provides an undercut region adjacent the receptacle, wherein the set-up tray also includes a container having a bottom support and a dome-shaped member that extends over the bottom support, wherein the bottom support extends beyond the member and presents two edge portions that are respectively received in the undercut regions, and wherein the container is opened by moving the dome-shaped member through the space between the projections.

27. An orthodontic patient set-up tray according to claim 26 wherein the substrate includes at least one additional projection, and wherein at least one additional projection includes an overhanging section.

28. An orthodontic patient set-up tray according to claim 26 wherein each projection includes an additional overhanging section that provides an undercut region adjacent an additional receptacle.

29. An orthodontic patient set-up tray according to claim 26 wherein the tray includes a first section and a second section, wherein the receptacle is located on the first section, wherein the second section includes an additional receptacle, and wherein the tray includes a coupling movably connecting the first section to the second section to enable relative movement between the first section and the second section.

30. An orthodontic patient set-up tray according to claim 29 wherein the coupling is a releasable coupling for selectively disconnecting the first section from the second section.

31. An orthodontic patient set-up tray according to claim 30 wherein the coupling comprises a hinge.

32. An orthodontic patient set-up tray according to claim 26, and further including a container received in the receptacle and an orthodontic appliance received in the container.

33. An orthodontic patient set-up tray according to claim 26 wherein the projections comprise elongated rails.

34. An orthodontic patient set-up tray according to claim 33 wherein the rails extend in directions generally parallel to each other.

35. An orthodontic patient set-up tray according to claim 33 and including a stop for limiting movement of the container.

36. An orthodontic patient set-up tray according to claim 35 wherein at least one rail includes an end portion that provides the stop.

* * * * *